United States Patent
Baets et al.

(10) Patent No.: US 9,488,583 B2
(45) Date of Patent: Nov. 8, 2016

(54) MOLECULAR ANALYSIS DEVICE

(71) Applicants: UNIVERSITEIT GENT, Ghent (BE); IMEC VZW

(72) Inventors: Roeland Baets, Deinze (BE); Ananth Subramanian, Ghent (BE); Nicolas Le Thomas, Ghent (BE)

(73) Assignees: UNIVERSITEIT GENT, Gent (BE); IMEC, Leuven (BE)

( * ) Notice: Subject to any disclaimer, the term of this patent is extended or adjusted under 35 U.S.C. 154(b) by 327 days.

(21) Appl. No.: 14/143,805

(22) Filed: Dec. 30, 2013

(65) Prior Publication Data

US 2014/0185042 A1 Jul. 3, 2014

(30) Foreign Application Priority Data

Dec. 31, 2012 (EP) ..................................... 12199795

(51) Int. Cl.
*G01J 3/44* (2006.01)
*G01N 21/65* (2006.01)
*G01N 21/552* (2014.01)

(52) U.S. Cl.
CPC ............ *G01N 21/658* (2013.01); *G01N 21/554* (2013.01); *G01N 2021/653* (2013.01); *G01N 2021/655* (2013.01); *G01N 2201/08* (2013.01)

(58) Field of Classification Search
CPC .................................................. G01N 21/658
USPC .......................................................... 356/301
See application file for complete search history.

(56) References Cited

U.S. PATENT DOCUMENTS

| | | | | |
|---|---|---|---|---|
| 4,395,126 A | * | 7/1983 | Kramer | G01N 21/645 250/228 |
| 4,797,842 A | * | 1/1989 | Nackman | G06T 17/20 345/420 |
| 5,828,450 A | * | 10/1998 | Dou | G01J 3/4412 250/339.07 |
| 9,140,543 B1 | * | 9/2015 | Allan | G01B 11/16 |
| 2003/0016434 A1 | * | 1/2003 | Torchigin | G02F 1/125 359/286 |
| 2006/0038990 A1 | | 2/2006 | Habib et al. | |

(Continued)

FOREIGN PATENT DOCUMENTS

WO 2006/027581 A1 1/2006
WO 2011/093879 A1 8/2011

OTHER PUBLICATIONS

European Search Report of EP 12199795.1.

*Primary Examiner* — Kara E Geisel
*Assistant Examiner* — Hina F Ayub
(74) *Attorney, Agent, or Firm* — Sughrue Mion, PLLC

(57) ABSTRACT

In the present invention, a molecular analysis device comprises a substrate, and a waveguide with a planar integrating element and filter or reflector element adjacent thereto is disposed on the substrate. The waveguide comprises a coupling means configured for coupling a predetermined frequency range of laser radiation into the waveguide. At least one metallic nanostructure is disposed on or adjacent to the planar integrating element, at least one metallic nanostructure is configured such that the field intensity and the gradient of the laser radiation, that is coupled into the waveguide, are enhanced over a sufficiently large volume around the nanostructure to simultaneously cause plasmonic based optical trapping of analyte(s) in a medium, and plasmonic based excitation of the particles to produce Raman scattered radiation. A Raman scattered radiation collection means is disposed on the substrate for collecting said Raman scattered radiation produced by the particles.

15 Claims, 12 Drawing Sheets

(56) References Cited

U.S. PATENT DOCUMENTS

| | | |
|---|---|---|
| 2006/0055922 A1 | 3/2006 | Li et al. |
| 2006/0164635 A1 | 7/2006 | Islam et al. |
| 2007/0165214 A1* | 7/2007 | Wu .......................... G01J 3/02 356/301 |
| 2008/0289965 A1* | 11/2008 | Engheta .................. B03C 5/005 204/547 |
| 2011/0024612 A1* | 2/2011 | Mintz ...................... G01J 1/08 250/252.1 |
| 2011/0122405 A1 | 5/2011 | Wu et al. |
| 2012/0212732 A1 | 8/2012 | Santori et al. |
| 2012/0281212 A1* | 11/2012 | Fattal .................. G01N 21/658 356/301 |
| 2014/0086522 A1* | 3/2014 | Adams ................ G02B 6/2813 385/3 |

* cited by examiner

MOLECULAR ANALYSIS DEVICE

TECHNICAL FIELD

The invention relates to molecular identification and/or analysis devices and methods for molecular identification and/or analysis using such devices.

BACKGROUND ART

Optical trapping using highly focused laser beam to trap and manipulate micro-particles and biological cells has been extensively studied and successfully demonstrated using conventional optical tweezers. The trapping in this case relies on the field gradient near the focus of the beam and therefore requires tightly focused beam(s) for stronger trap. This is achieved using costly high numerical aperture (NA) lenses and a bulky microscopic system. However the trapping volume is limited in such systems. Besides, the high intensity in the focus makes it unsuitable for several biological species. To overcome this problem trapping based on the evanescent wave at the interface of two dielectric media, such as planar waveguides has gained lots of interest. Here, the trapping is achieved due to the intensity gradient of the evanescent wave extending into the cladding region and particles are trapped on top of the waveguide surface. This can be achieved at relatively low power and also provides the ability to transport particles over large distances (due to the radiation pressure of the guided light) to a desired region of interest.

Optical tweezers generally suffer from high intensity at the focus, use of expensive bulk optics, and diffraction limited focus leading to difficulty in trapping sub-100 nm particles. Waveguide trapping requires high input power (to overcome coupling and waveguide losses) and has problems overcoming both the radiation pressure of the guided light and Brownian motion of the particles to provide a stable trap at a specific location. The plasmonic based optical trapping addresses most of these issues and provides a stable trap for particles and biological cells from a few nm to hundreds of nm. It has a low power threshold, and can be easily integrated with the waveguide and microfluidics.

Measor et al., "On-chip surface-enhanced Raman scattering detection using integrated liquid-core waveguides", Applied Physics Letters, 90, 211107, 2007 discloses on-chip detection of analyte using surface enhanced Raman scattering (SERS), using liquid core anti resonant reflecting optical waveguides (ARROW). This did not involve trapping of particles but a combination of microfluidics and in-situ optical probing of particles inside the core of the waveguides. The analytes along with Silver nanoparticles were guided along the liquid core section and the optical wave was guided on the $Si_3N_4$ layer above that probed the particles flowing in the liquid core section underneath. Silver nanoparticles used enhanced the Raman scattering and generated SERS that was detected at the output of the waveguide. The output was collected using an objective at the other end and fed to Raman spectrometer for spectral analysis.

On-chip optical trapping and fluorescence detection was performed by Kuhn et al., "Loss-based optical trap for on-chip particle analysis", Lab Chip, 9, 2212, 2009, using a combination of liquid and solid core waveguides. Particles were trapped using a loss based dual beam trapping mechanism. The particle is trapped by the counter propagating beams and asymmetric loss profile along the waveguide. The liquid core delivers the particles to the trap region and then it is excited using another laser. The fluorescence is collected by the orthogonal waveguide.

WO 2006/081566 A1, WO 2006/081567 A1 and U.S. Pat. No. 7,151,599 B2 relate to on-chip Raman spectroscopy using plasmonic enhancements and integrated light sources and detectors. The basic design described comprises of analytes placed on a Raman enhancement (RE) structure (metallic element ranging from monolithic layer to nanoparticles, dots, wires) which itself is positioned in a cavity formed on the waveguide guiding the laser light. The laser source irradiates the RE structure and analyte (directly through waveguide end or indirectly through evanescent field emanating from the waveguide surface), producing an enhancement effect. This occurs due to the radiation impinging the RE structure produces strong electromagnetic field in the RE structure and the analyte which is in close proximity is irradiated by this enhanced field producing strong Raman scattered photons.

WO 2011/093879 A1 discloses a molecular analysis device composed of a self-collecting substrate for surface enhanced Raman spectroscopy, comprising a waveguide layer on a substrate, the waveguide layer comprising coupling means and a metallic nanostructure to cause both plasmonic based optical trapping and plasmonic based excitation of analytes in a medium.

US 2012/0212732 A1 describes a SERS system with nano-fingers to trap analyte molecules and providing hot-spots of large electric field strength, causing the analyte molecules to emit Raman scattered light. The light source, waveguide structure, Raman detector and collecting optics are arranged on a single chip.

DISCLOSURE OF THE INVENTION

It is an aim of this invention to provide an on-a-chip molecular analysis device based on the simultaneous optical trapping and SERS whereby excitation, detection and collection of Raman scattered radiation from a single or multiple analytes over a wide wavelength range can be performed while maintaining low power operation, for material systems ranging from low to very-high index contrast (both laterally and vertically).

According to the present invention, the aforementioned aim is achieved with the device of claim 1. The molecular analysis device comprises a substrate, and a waveguide on the substrate. The waveguide comprises a coupling means configured for coupling over a predetermined frequency range of laser radiation into the waveguide and a planar integrating element with a reflector or filter element adjacent to the planar integrating element, for example a reflector along the surface (periphery) of the planar integrating element or inline with the planar integrating element. The waveguide and the planar integrating element have a height such that the waveguide remains single mode out-of-plane. At least one metallic nanostructure is provided on or adjacent to the planar integrating element. This at least one metallic nanostructure is configured such that the field intensity and the gradient of the laser radiation, that is coupled into the waveguide, are enhanced over a sufficiently large volume around the nanostructure to simultaneously cause plasmonic based optical trapping of analytes in a medium, and plasmonic based excitation of particles to produce Raman scattered radiation. A Raman scattered radiation collection means may be disposed on the substrate for collecting the said Raman scattered radiation produced by said particles.

With the device according to the invention, low power operation can be achieved by the combination of waveguide confinement due to a high vertical-index-contrast (VIC) and reflection in the planar integrating element and the plasmonic enhancement due to metallic nanostructures can produce sufficient light intensity to simultaneously trap and generate SERS signal from the analyte(s) even at low power input laser radiation.

Furthermore embodiments of the present invention can also lead to an enhanced and better collection efficiency of Raman scattered radiation from a trapped particle by the waveguide based collection system described herein for a range of waveguide designs and materials with low-to-very-high lateral index contrast (LIC) systems.

With the invention, high signal-to-noise ratio can be achieved since the metallic nanostructures can produce very large optical forces that provide stable and very localized optical trapping of analyte(s) which can lead to much lower thermal drift, higher intensity, quenching of the background florescence from the analyte(s) occurring at the same excitation wavelength thereby lowering the noise floor, and longer integration time due to very stable trap for collecting the scattered Raman radiation from a single or multiple analytes.

In embodiments according to the invention the signal-to-noise ratio can be further improved by making the reflector along the periphery of the integrating element sufficiently narrowband to suppress or filter a higher fraction of Rayleigh scattered radiation from the analyte(s).

The analyte may be brought in contact with the metallic nanostructure, for example in the following ways: the device may be immersed in a solution, or microfluidics may be used where the analytes are pumped in over the region of plasmonic design and pumped out after analysis, or in other ways known to the person skilled in the art.

In embodiments according to the invention, the planar integrating element may consist of a slab, e.g. a broadened part of the waveguide which can be for example a disk or a section of a disk (a "planar integrating sphere") or a polygonal element, as will be described in embodiments of the present invention, or a waveguide section adjacent to an inline filter or reflector element, as will be described in other embodiments of the present invention, but is not limited thereto.

In embodiments according to the invention, the waveguide may be made of (but not limited to) a high-refractive-index material.

In embodiments according to the invention, the at least one metallic nanostructure may consist of one or more of the following: a disc, nano-rods or nanotips having different shapes such as triangle, polygon, rectangle, square etc; nano-voids or apertures, metallic nanoparticles in a colloidal suspension, or any other appropriate metallic nanostructure known to the person skilled in the art. Further, the different types of nanostructures may be made of gold, silver, copper, aluminium, chromium, lithium, tin, or any other material known to the person skilled in the art.

In embodiments according to the invention, the metallic nanostructure may be configured for transforming the underlying waveguide mode to an intensity profile that forms a stable trap by overcoming the random Brownian motion requiring a potential energy barrier of at least 10 $k_bT$, wherein $k_b$ is the Boltzmann's constant and T is the temperature in the vicinity of the particles/metallic nanostructure interface. In this way, Brownian motion of the particles can be overcome.

In embodiments according to the invention, a laser source may be disposed on the substrate and configured for generating said laser radiation. In embodiments according to the invention, a radiation analyser may be disposed on the substrate and configured for analysing said collected Raman scattered radiation. In this way, an integrated on-a-chip solution can be achieved.

In embodiments according to the invention, the coupling means may be a grating coupler or taper and/or the collection means may comprise an optical structure disposed adjacent to said metallic nanostructure.

In embodiments according to the invention, the metallic nanostructure may be disposed on the planar integrating element, and another waveguide may be connected to the planar integrating element, the second waveguide comprising a grating coupler designed for Stokes and/or Anti-Stokes wavelength.

In embodiments according to the invention, the reflector along the surface of the integrating element may be a distributed Bragg reflector (DBR), a metallic mirror or a total internal reflection mirror in the case of a wire waveguide, or the reflector may be simply the single interface between the slab waveguide and the outer lateral cladding, e.g. reflection due to the difference in refractive index of the waveguide and the refractive index of the outer cladding region.

In embodiments according to the invention, the waveguide may comprise an arrayed waveguide grating (AWG) section where the metallic nanostructure is disposed, the AWG length being configured such that the Stokes and Anti-Stokes wavelengths are focused at different regions of the waveguide, and wherein the waveguide comprises grating couplers at both ends to couple said laser radiation into and said Raman scattered radiation out of said waveguide.

BRIEF DESCRIPTION OF THE DRAWINGS

The invention will be further elucidated by means of the following description and the appended drawings.

MODES FOR CARRYING OUT THE INVENTION

Figure 1:
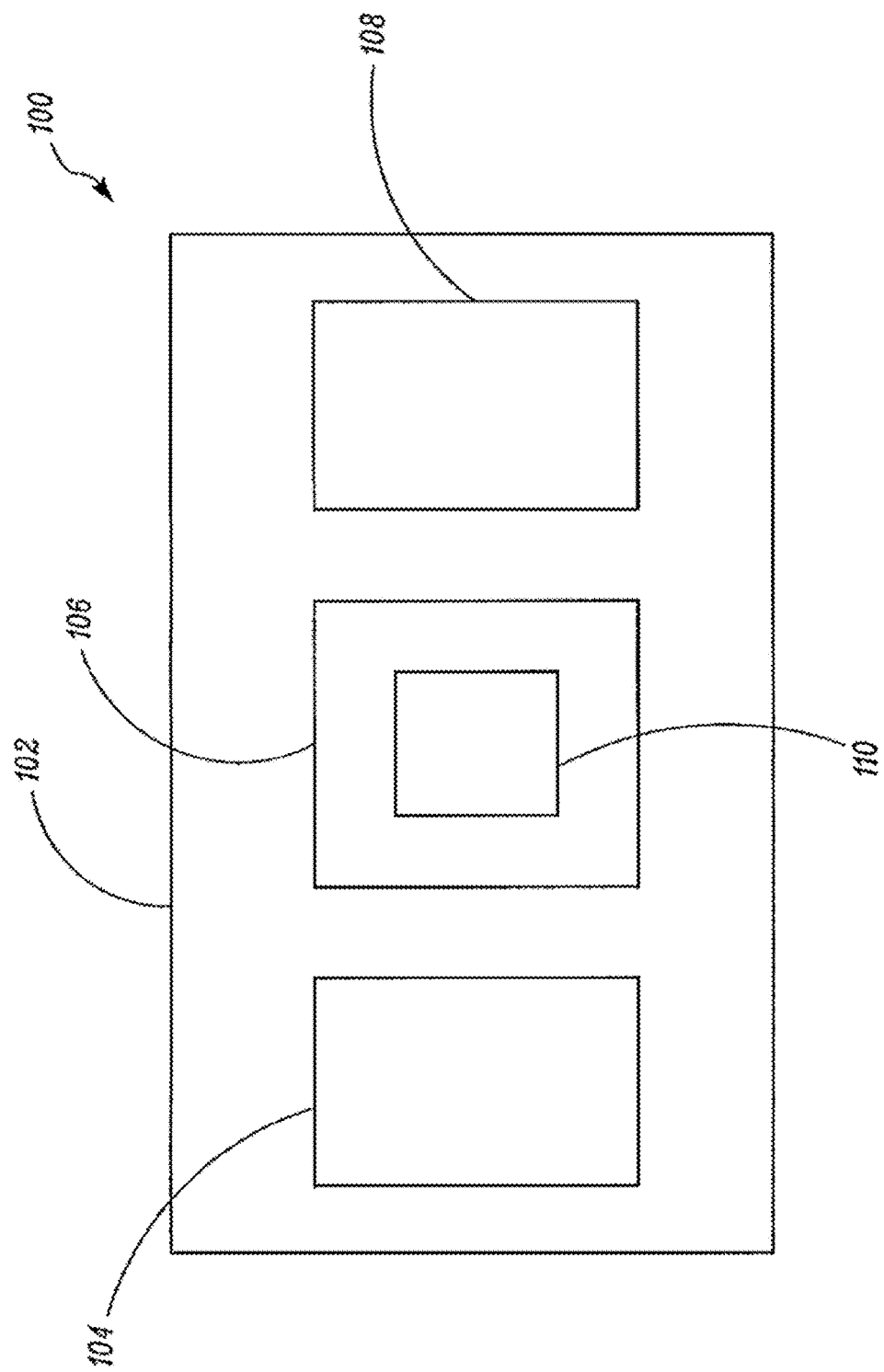
FIG. 1 shows a schematic view of a molecular analysis device, according to an embodiment of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

The term "comprising" used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Depending on the geometry of the metallic nanostructure used plasmonic interaction with the incident light takes place due to the excitation of localized surface plasmons (LSPs). LSPs are basically the bound electron plasmas associated with particles, nano voids (smaller than the incident wavelength) and they can be coupled directly to the propagating light. Upon excitation the resonance causes huge jumps in the electric field intensity leading to "hot-spots" close to the surface. This enhancement not only comes from the intensity enhancement but also due to strong localization of the electric field to a very small area much smaller than diffraction limit. This leads to a strong intensity gradient that is responsible (more so than compared to enhancement in the field intensity) for large optical forces and trapping of the particle when it comes in the vicinity of such hot-spots. However, the hot-spots are strongly dependent on design, shape, surrounding medium, metal used etc and based on these characteristics only certain wavelengths can generate these hot-spots and hence optical trapping. This can be achieved by tailoring the dispersion characteristics of waveguide-metal structure for resonance phase matching.

Raman spectroscopy is an ideal optical detection technique for chemical and biological species. The Raman signal is the fingerprint signature of the chemicals and bio-molecules as it represents the vibrational frequencies of the bonds present in the molecules. It also enables to detect and identify non-fluorescent samples and therefore is considered to be a label-free and foolproof technique for characterizing molecular structure as compared to other techniques such as absorption and florescence spectroscopy. Raman scattering occurs at all wavelengths but is stronger at shorter wavelengths. However the Raman scattering is a highly inefficient process with low scattering cross section that makes detection of the signal extremely difficult and to have high sensitivity the scattered intensity should be enhanced. This can be done by different processes and among them surface enhanced Raman scattering (SERS) is the most widely used technique.

The SERS technique consists of locating the target analytes within nanometer range of roughened metal surfaces or metal nanoparticles. The exact phenomenon behind SERS is still under debate but the presence of the metal surface or nanoparticles provides a tremendous enhancement to the resulting Raman signal. This is through an electromagnetic enhancement of both the excitation light and Stokes-shifted light, as well as through electrochemical interactions between the analyte and the metal. Often, this measured enhancement is considered to be a modification to the effective Raman scattering cross-section. Enhancements to the effective Raman scattering cross-section of up to 14 orders of magnitude have been demonstrated.

In the context of this invention, the terms "radiation" and "light" are used for indicating electromagnetic radiation with a wavelength in a suitable range, e.g. electromagnetic radiation with a wavelength that is transparent in the waveguide but leads to strong Raman scattering at Stokes and anti-Stokes wavelength by the analyte under investigation.

In the present invention, a molecular analysis device based on simultaneous optical trapping and surface enhanced Raman scattering is provided.

A molecular analysis device 100, according to embodiments of the present invention, comprises a substrate 102, as shown in FIG. 1. The molecular analysis device 100 may be used to study a single or multiple analytes. A laser source 104, a waveguide 106, and a radiation analyser 108 are disposed on the substrate 102. The waveguide 106 may comprise a coupling means (not shown in FIG. 1) configured to couple a predetermined frequency range of laser radiation into the waveguide 106. Further, an enhancement structure 110 is disposed on the waveguide 106. In various embodiments of the present invention, the enhancement structure 110 may comprise a single monolithic layer, such as, a roughened surface. In other embodiments of the present invention, the enhancement structure 110 may comprise one or more discrete elements. The one or more discrete elements may be metallic nanostructures, such as, nano-rods or nanotips having different shapes such as triangle, polygon, rectangle, square etc, nano-voids or apertures, metallic nanoparticles in a colloidal suspension etc. Further, the different types of nanostructures may be made of gold, silver, copper, aluminium, chromium, lithium, tin etc. The enhancement structure may optically trap one or more particles of an analyte.

The radiation analyser 108 comprises one or more Raman scattered radiation collection means (described hereinafter as "the collection means"). The one or more collection means are configured to collect radiation from the one or more particles trapped by the enhancement structure 110. The radiation analyser 108 may be used to detect and/or analyse one or more parameters of the analyte(s) being studied by the molecular analysis device 100 based on the radiation collected by the collection means. The radiation analyser 108 comprises various other components for analysis, for example, but not limited to, spectrometer, optical filters, radiation sensors, optical amplifiers etc. Various alternative embodiments of the metallic nanostructures and collection means are described in detail in conjunction with FIGS. 3-12.

The substrate 102 may be made of silicon or any other similar material. The various components disposed on the substrate 102, such as the laser source 104, the waveguide 106, and the radiation analyser 108 may be integrated into the substrate 102 as part of a monolithic integration. The substrate 102 may also comprise additional integrated circuits for performing various functions. The molecular analysis device 100 therefore is a fully integrated on-chip molecular analysis device which may be compact, cost and energy efficient, and user friendly as compared to prior art analysis devices.

Further, the laser source 104 may be a single wavelength or tunable laser diode, which emits a laser radiation with a wavelength that is effective for optical trapping and SERS. In embodiments of the present invention, the laser radiation may be in the visible to mid-infrared range, from about 500 nm to 1100 nm.

Figure 2:
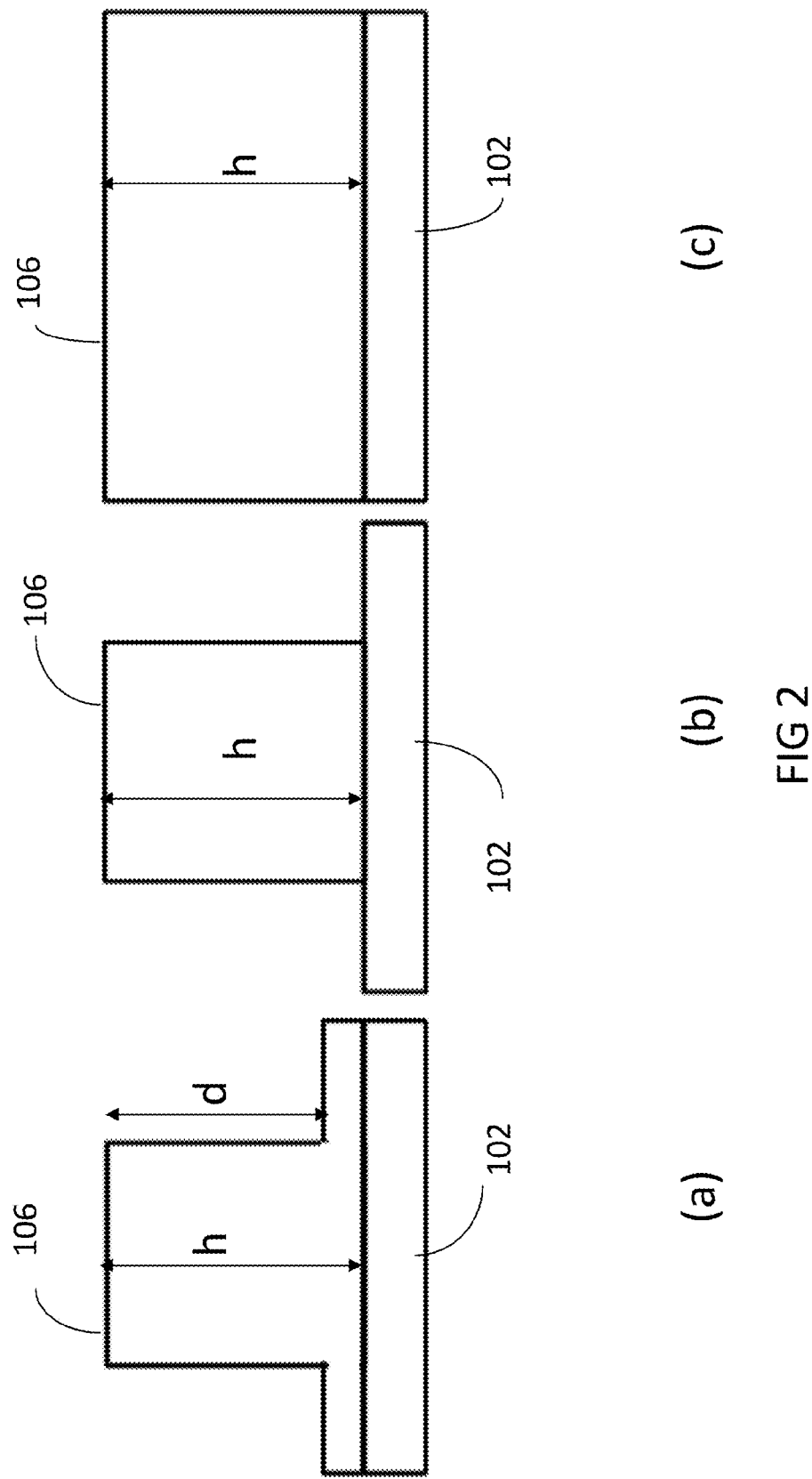
FIG. 2 shows the schematic cross-section of the different waveguide geometries leading to different kind of lateral and vertical index contrast systems.

FIG. 2 depicts the different waveguide geometries leading to different index contrast. The index contrast is present in both the vertical (out-of-plane) and lateral (in-plane) direction. The present invention targets the material systems with high to very-high vertical-index-contrast (VIC) systems such as $Al_2O_3$, $Si_3N_4$, Si etc with respect to the underlying cladding layer (e.g. $SiO_2$). The height of the waveguide (h) is chosen to ensure single mode operation in vertical direction (out-of-plane). The lateral-index-contrast (LIC) is determined by various factors: nclad (index of the upper cladding), etch depth and the core material index. The highest LIC can be achieved in the case of completely etched system (strip waveguide) and air cladding (FIG. 2b). Examples of very high-index-contrast strip waveguide systems include Si, diamond, silicon carbide etc. In the strip waveguide, the lateral confinement and single mode behavior can also be controlled by the width of the waveguide. In the case of a rib waveguide or partially etched waveguide (FIG. 2a), the etch depth (d) dictates the width of the waveguide and also the LIC. The slab waveguide (FIG. 2c) confines light only in vertical direction. The LIC is defined in terms of the capture angle or the numerical aperture of the waveguide. For the fully etched and slab waveguide systems, as shown in FIGS. 2b and 2c, the capture angle is calculated using $(\sin^{-1}(\sqrt{n1_{eff}^2 - nclad^2})/n1_{eff})$ where $n1_{eff}$ is the effective index of the completely etched waveguide core and nclad is the index of the upper surrounding region. For partially etched waveguide systems, as shown in FIG. 2a, the capture angle is calculated using $\sin^{-1}(\sqrt{n1_{eff}^2 - nclad_{eff}^2})/n1_{eff}$, where $nclad_{eff}$ is the effective index of the side-clad region in FIG. 2b. The waveguide (material) systems with capture angle <25 degrees are termed as low LIC systems, for capture angle in the range of 25-50 degrees as medium-high LIC systems and for capture angle is in the regime of 50-90 degrees as very-high LIC systems.

Various alternative embodiments of the molecular analysis device 100 will be described hereinafter with reference to FIGS. 3-12.

Figure 3:
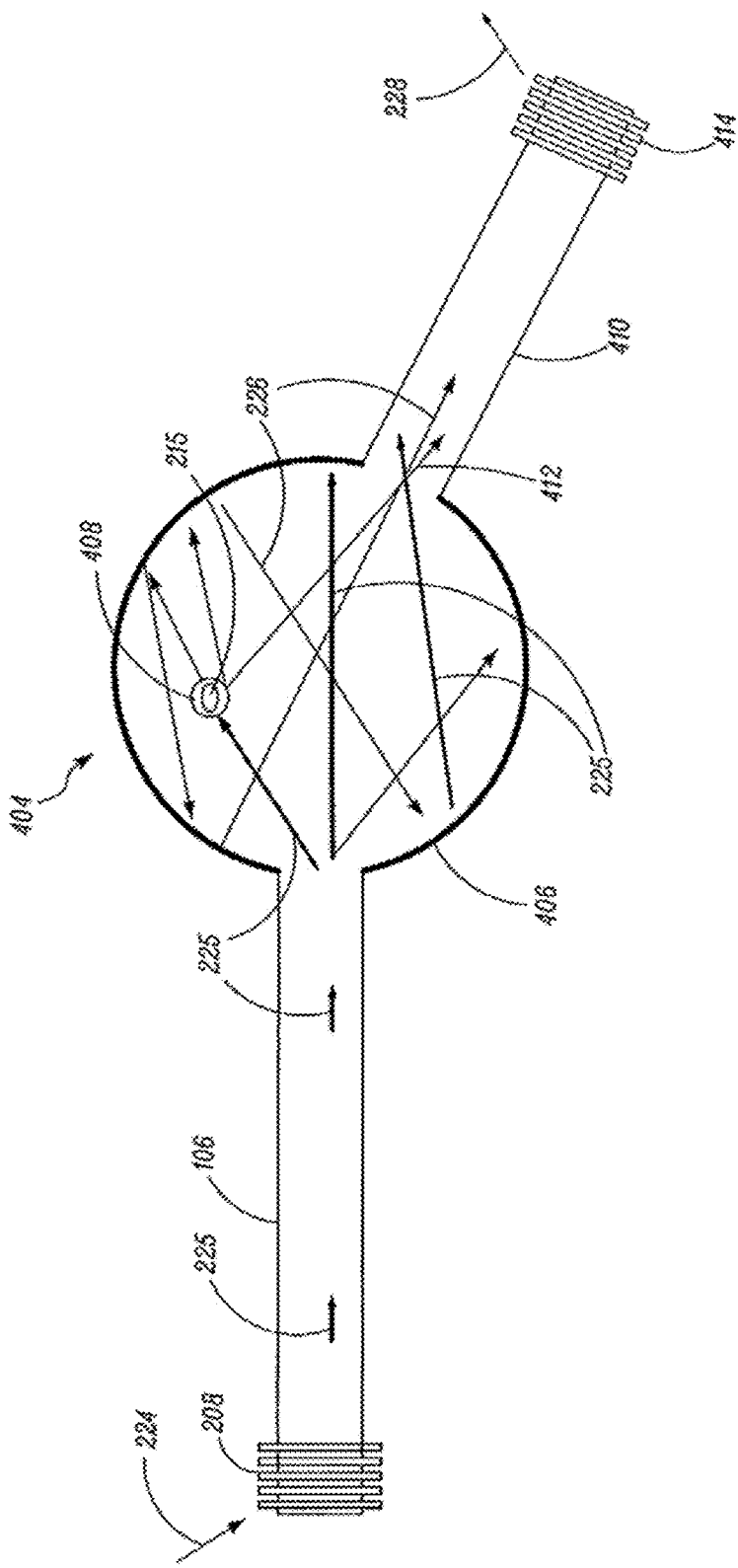
FIG. 3 shows a sectional view of the waveguide with a planar integrating sphere, according to an embodiment of the present invention.

FIG. 3 shows the waveguide 106, according to an embodiment of the present invention. The waveguide 106 comprises a planar integrating sphere 404 (described hereinafter as "the sphere 404"). The planar integrating element may have alternate shapes, for example, polygonal (described with reference to 15 FIG. 4). A distributed Bragg reflector 406 (described hereinafter as "the Bragg reflector 406") is provided along the surface of the sphere 404. In an embodiment, the sphere 404 may be a slab made of Si3N4. The Bragg reflector 406 is configured for substantial specular reflection of all incident radiation at all locations. The Bragg reflector 406 may comprise various alternating layers 20 perpendicular to the normal of the surface of the integrating element, having low refractive index and high refractive index in order to achieve this. Further, a gold disc 408, disposed on the sphere 404, is embodied as a first type of metallic nanostructure. The gold disc 408 is configured to trap one or more particles 215 of the analyte. The particle 215 is trapped on the gold disc 408. The trapping 25 metallic element 408 is not limited to the gold disc and may be comprised of any other design without departing from the scope of the present invention, e.g. gold nanorods or nano-tips but not limited thereto.

Another waveguide 410 is connected to an exit opening in the sphere 404. The waveguide 410 is configured as a collecting means and is coupled to the only exit 412 of the sphere 404. In an embodiment, the waveguide 410 may be made of $Si_3N_4$. The waveguide 410 comprises a grating coupler 414 configured to allow passage of Stokes wavelength and block the pump wavelength. In alternative embodiments, multiple exit openings may be provided in the sphere with multiple waveguides 410 connected thereto as collecting means.

In operation, the excitation laser radiation 225 enters the sphere 404 and irradiates the gold disc 408. The gold disc 408 causes localised enhancement of the intensity of the laser radiation 225 due to surface plasmons. The Raman scattered radiation 226, from the particle 215 trapped on the gold disc 408, and the excitation laser radiation may undergo multiple reflections from the Bragg deflector 406. Each time the reflected excitation laser radiation hits the gold disc 408 it leads to further enhancement and subsequent re-emission of Raman scattered radiation. Subsequently, the Raman scattered radiation 226 enters the waveguide 410 though the only exit 412 of the sphere 404. The Raman scattered radiation 226 then passes through the grating coupler 414. The grating coupler 414 allows passage of the Stokes radiation 228 and filters out the wavelength of the laser radiation 225. The Stokes radiation 228 from the grating coupler 414 may be sent to the radiation analyser 108.

Figure 4:
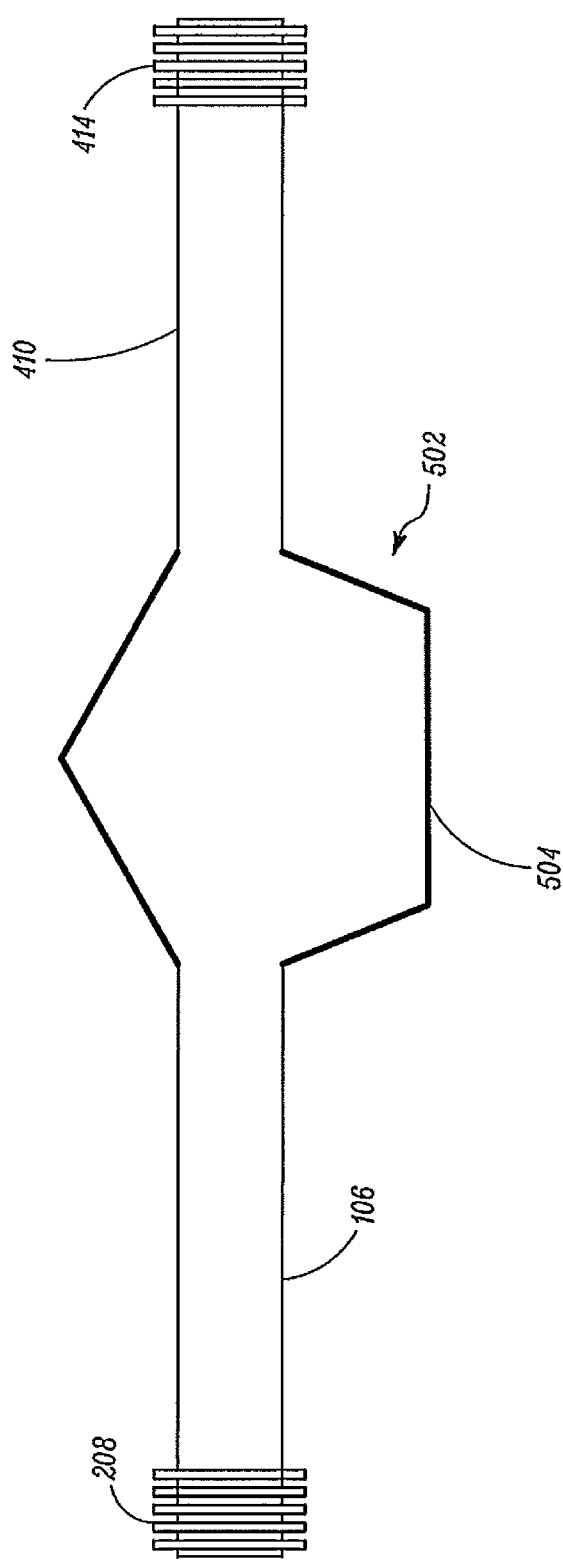
FIG. 4 shows a sectional view of the waveguide with a polygonal planar integrating element, according to an embodiment of the present invention.

FIG. 4 shows the waveguide 106, according to another embodiment of the present invention. The waveguide 106 comprises a polygonal planar integrating element 502 (hereinafter described as the "polygonal element 502"). The polygonal element 502 may comprise a Bragg reflector 504 along the surface. The waveguide 410 is connected to the polygonal element 502. The operation of the polygonal element 502 along with the waveguides 106 and 410 is similar to the embodiment described with reference to FIG. 3.

Figure 5:
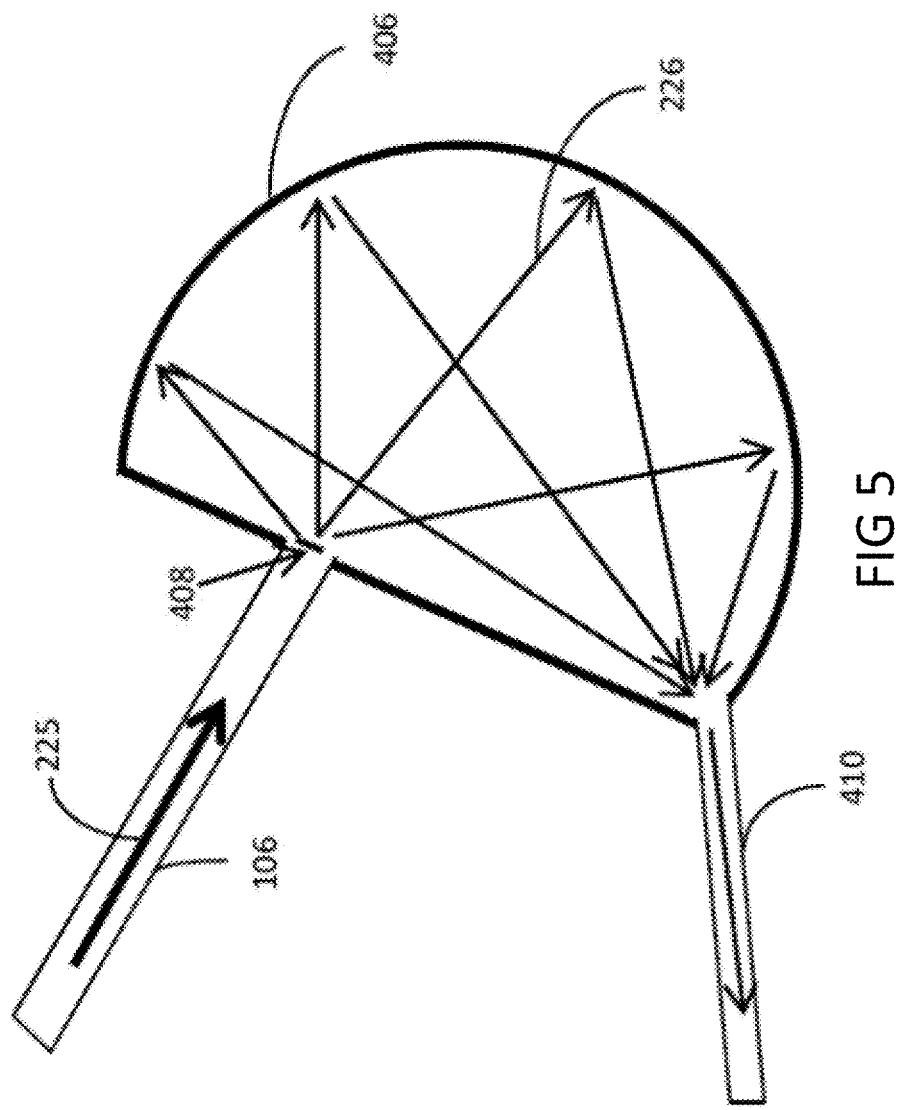
FIG. 5 shows a top view schematic of the planar integrating sphere for optical trapping and SERS collection.
Figure 6:
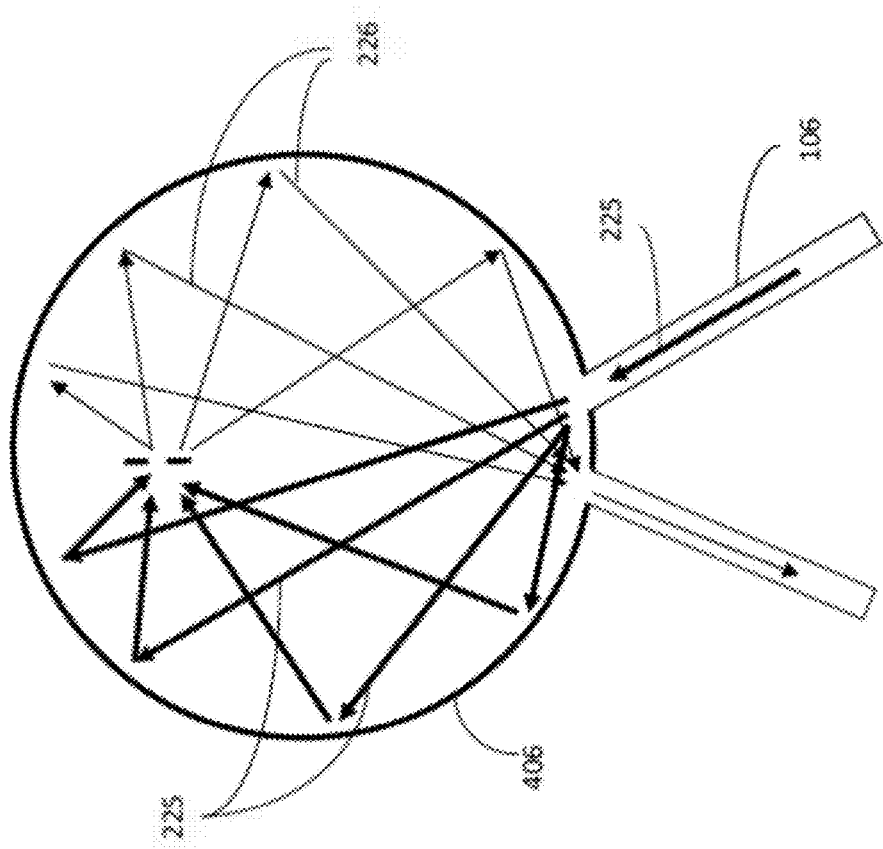
FIG. 6 shows a top view schematic of the planar integrating sphere for optical trapping, SERS collection and excitation.
Figure 7:
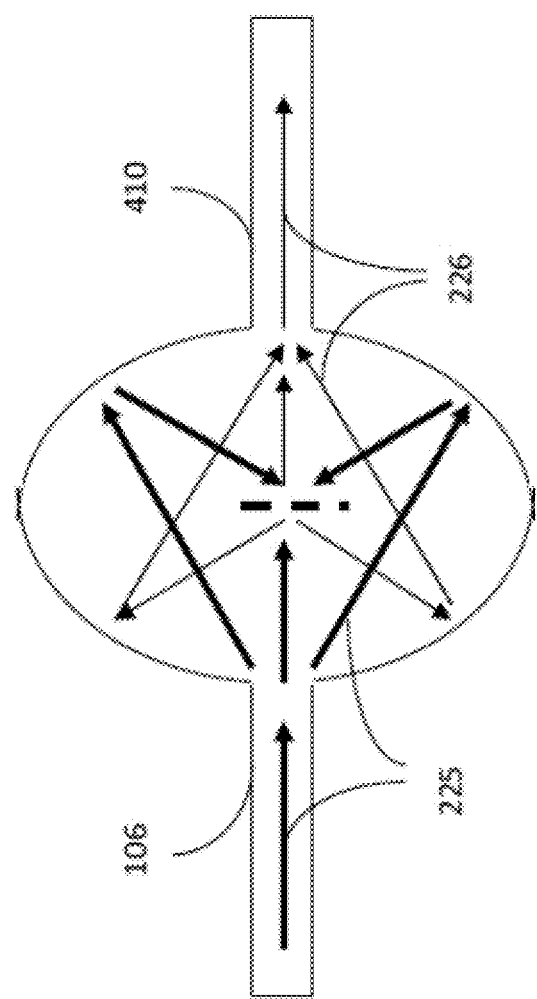
FIG. 7 shows a top view schematic for excitation and collection from an integrated waveguide and integrating sphere.

FIGS. 5, 6 and 7 show other possible embodiments of the integrating sphere 404. The radiation emitted by the metallic nanostructure is omnidirectional and the waveguide 106 has a limited numerical aperture, therefore to capture all the light and direct it towards the output waveguide 410 an integrating element is provided that can image with angular demagnification and hence lateral magnification. The off-axis arrangement helps to spatially separate input and output waveguides.

In FIG. 5, a planar integrating element comprising a disc segment is provided, wherein the incoming waveguide 106 broadens abruptly into a slab at the point of the metallic nanostructure 408. The Raman scattered light is coupled to the slab mode as a diverging spherical wave. This spherical wave hits a curved reflector in an off-axis way. This reflector turns the diverging wave into a converging spherical wave. This converging spherical wave focuses in a point of the slab where the slab transforms back into a photonic waveguide 410. The magnification is chosen so as to optimize the coupling to this wire. It is worth noting that the design preferably is such that the reflection off the outer boundary of the integrating sphere 404 is not a Lambertian but a specular reflection. This specular reflection preferably is to be designed to be strong for a specific angle of incidence in every location. In case of high lateral index-contrast, the reflector may be simply the single interface between the slab and the lateral cladding. In lower index cases, it may be a Distributed Bragg Reflector 406 (or quarter wavelength stack) structure with enough periods so as to provide strong reflection.

In FIG. 6, a disc-shaped planar integrating element is provided. Here, the same scheme is modified for excitation as well as collection from the metallic nanostructure. Here the input waveguide mode is imaged onto the metallic nanostructure and the metallic nanostructure is imaged onto the output waveguide 410. The same structure can be modified and taken one step further, turning the curved reflector for collection (right hand part of FIG. 6) into a curved grating and hence turn the structure immediately into an echelle grating demultiplexer with an array of output waveguides. This will convert the device into an integrated Raman spectrometer with all the advantages of a waveguide, optical trapping and nanometallic plasmonic element all in one design.

In the alternative embodiment of FIG. 7, a planar integrating element of oval shape is provided and the input waveguide 106 and output waveguide 410 are in line. This has the disadvantage that some of the pump light is immediately passed on to the output waveguide 410—implying the need of further spectral filtering downstream—but also has major advantages as explained below. In this configuration there is no freedom for the choice of magnification, contrary to the case of FIGS. 5 and 6. Simple design rules can be derived by assuming a paraxial approximation and spherical surfaces (even if a real optimized device will have an aspherical shape). From the simple geometrical optics relation for reflective imaging one can write s=(¾)R, where s is the distance between the metallic nanostructure and the input waveguide 106 and output waveguide 410 respectively. R is the radius of curvature of the reflector. From the same relation, one can also notice that such a design automatically ensures that for the excitation case there is a lateral magnification of 0.5 (angular magnification of 2) whereas for the collection case there is 2× lateral magnification (angular magnification of 0.5). Such a geometry is useful for the high-lateral-index-contrast cases (mostly for the range 25 degrees<capture angle<50 degrees) where the advantage of an in-line reflector system boosts the collection efficiency. This structure can be scaled down to a very compact structure where all dimensions (the waveguide width, the length, the reflector dimensions) are of the order of the vacuum wavelength of light.

In order to improve the collection efficiency, the reflecting structure in any of the embodiments can be designed (for e.g. multi-stacks of DBR) to have a narrowband of reflection spectrum thereby rejecting a higher fraction of Rayleigh scattered radiation reaching an output waveguide.

Figure 8:
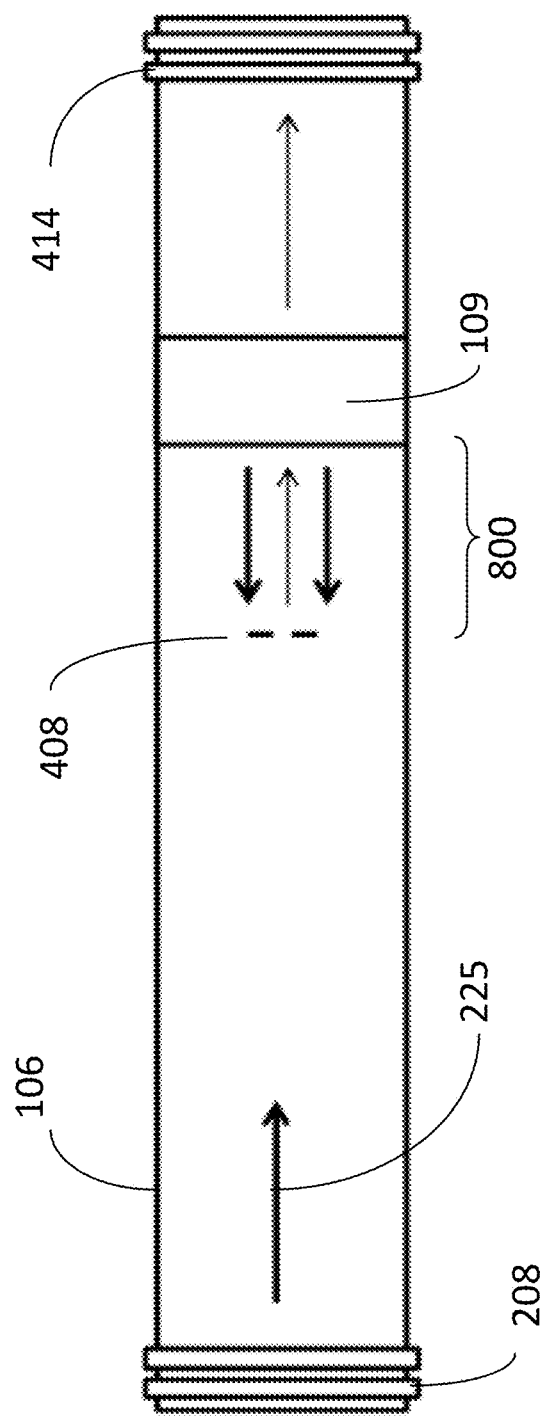
FIG. 8 shows a top-view schematic of a simple waveguide (wire) for excitation and collection of SERS signal for the case of a very high lateral and vertical index contrast system, according to an embodiment of the present invention.

FIG. 8 shows the waveguide 106, according to another embodiment of the present invention, for waveguide systems with very high lateral and very high vertical index contrast. The planar integrating element for collection may in this case be simply a section 800 of the waveguide wire. Both vertical and lateral high index contrast is advantageous for enhanced excitation and collection of the Raman radiation and the stronger but shorter evanescent tail of the guided mode ensures higher trapping stiffness in the small volume around the plasmonic antennas. The metallic nanostructures may be gold bow-tie antennas but are not limited thereto. The waveguide may comprise coupling means for input and output radiation. In addition, it may comprise inline filters 109 to reject Rayleigh scattered radiation and to send back the pump radiation that can re-excite the SERS from the trapped analytes.

Figure 9:
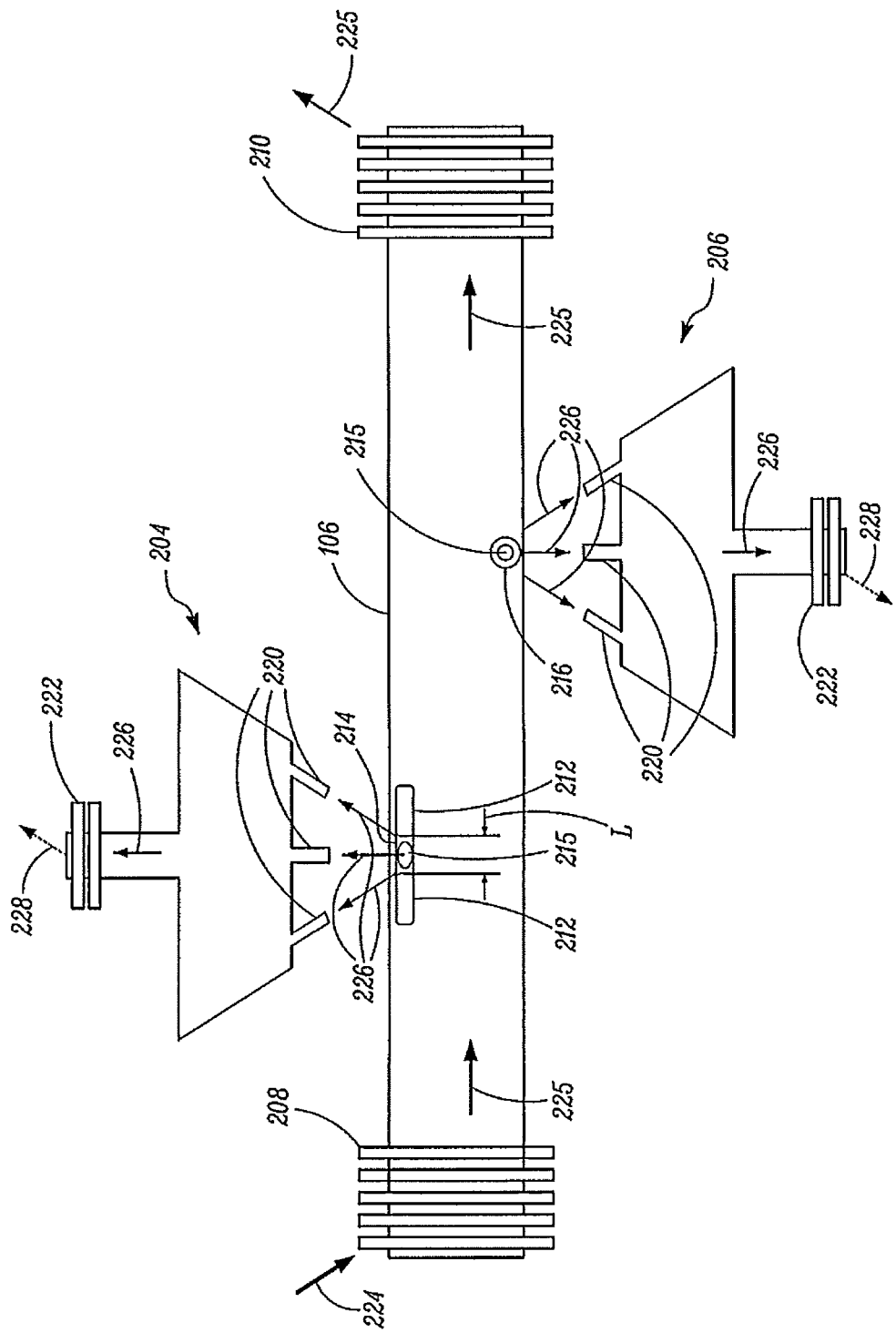
FIG. 9 shows a sectional view of a waveguide and collection means, according to an embodiment of the present invention.

FIG. 9 shows the waveguide 106, and collection means 204 and 206, according to an embodiment of the present invention (the integrating element is not shown in this figure, but it is to be understood that in this embodiment an integrating element according to one of the above described embodiments is provided). The waveguide 106 may be a high-vertical-refractive-index-contrast waveguide providing a compact structure, and improved confinement of radiation. In various embodiments of the present invention, the waveguide 106 may be single-mode waveguide in the form of a wire made of silicon nitride ($Si_3N_4$). Further, a coupling means 208 is embodied as a grating coupler. The waveguide 106 also comprises an exit grating coupler 210.

Two gold nano-rods 212 are embodied as a type of metallic nanostructure. The gold nano-rods 212 are configured to trap one or more particles of the analyte between them in a trapping region 214. In FIG. 9, a single particle 215 is shown to be trapped between the gold nano-rods 212. However, multiple particles may also be trapped in the trapping region 214. The particles may be cells, viruses, DNA, any other biomolecules, nanoparticles etc. In an embodiment of the present invention, each gold nano-rod 212 may have a height in a range from about 30 nm to 200 nm. Further, a length L of the trapping region 214 may be in a range from about 2 nm to 150 nm. In various embodiments, multiple pairs of gold nano-rods 212 may be provided.

A gold disc 216 is embodied as another type of metallic nanostructure. The gold disc 216 is configured to trap one or more particles of the analyte. In FIG. 9, the particle 215 is shown to be trapped on the gold disc 216. In an embodiment of the present invention, the gold disc 216 may have a thickness in a range from about 30 nm to 200 nm. Further, the gold disc 216 may have a diameter in a range from about 100 nm to 5 µm. In various other embodiments of the present invention, multiple gold discs 216 may be provided. However, the metallic nanostructures 212 and 216 may be of any other design within the above said dimensions without departing from the scope of the present invention.

The different types of metallic nanostructures are disposed on the waveguide 106 by various processes. For example, the gold nano-rods 212 and the gold disc 216 may be deposited on the waveguide 106 by various deposition techniques, such as, electron-beam physical vapour deposition, thermal evaporation, or the like. Alternatively, the gold nano-rods 212 and the gold disc 216 may be patterned on the waveguide by various processes, such as, electron-beam lithography, nano-imprint lithography, or the like.

The collection means 204 and 206 are adjacent to the gold nano-rods 212 and the gold disc 216, respectively. The collection means 204 and 206 may be high-vertical-refractive-index-contrast waveguides providing a compact structure, improved confinement of radiation and collection efficiency. In an embodiment of the present invention, each of the collection means 204 and 206 comprises an optical structure in the form of a multi-mode interference (MMI) type waveguide that may be made of silicon nitride ($Si_3N_4$). As shown in FIG. 9, each of the collection means 204 and 206 has a substantially trapezoidal cross-section. However, the collection means 204 and 206 may be of any cross-section without departing from the scope of the present invention. Further, each of the collection means 204 and 206 comprise multiple collecting rods 220. The collecting rods 220 protrude from the trapezoidal region of each of the collection means 204 and 206 towards the waveguide 106. The collecting rods 220 may improve collection of radiation from the trapped particles 215. Further, grating couplers 222 are provided near the exits of the collection means 204 and 206. The grating couplers 222 are configured to allow passage of Stokes wavelength and filter out the pump wavelength (wavelength of the laser radiation).

In operation, laser radiation 224 from the laser source 104 is coupled into the waveguide 106 by the coupling means 208. Laser radiation 225 inside the waveguide 106 irradiates the gold nano-rods 212 and the gold disc 216 disposed on the waveguide 106. Consequently, the gold nano-rods 212 and the gold disc 216 cause localised enhancement of the intensity and a strong intensity gradient of the laser radiation 225 due to LSPs. In various embodiments of the present invention, the gold nano-rods 212 and the gold disc 216 may be disposed within depressions (not shown) on the waveguide 106 to improve enhancement of the laser radiation 225. The enhancement of the field occurs over a predetermined, sufficiently large volume to cause both plasmonic based optical trapping of the particles 215 of the analyte, and plasmonic based excitation of the particles 215 to produce Raman scattered radiation 226, leading to a stable trap. Therefore, the Raman scattered radiation 226 is generated by SERS. For example, the gold nano-rods 212 and the gold disc 216 are configured for transforming the underlying guided mode of the laser radiation 225 to an intensity profile that forms the stable trap by overcoming the random Brownian motion of the particles of the analyte. This requires a potential energy barrier of about 10 $k_bT$, wherein $k_b$ is the Boltzmann's constant and T is the temperature of the particles.

The Raman scattered radiation 226 is collected by the collection means 204 and 206. The grating couplers 222 filter out the laser radiation 225 and permit only Stokes radiation 228 to pass. The Stokes radiation 228 may be sent to the radiation analyser 108 for detection and/or analysis of the trapped particles 215. In an embodiment, the laser radiation 225, passing out of the exit grating coupler 210, may also be sent to the radiation analyser 108.

Thus, plasmonic based Raman excitation and optical trapping is obtained by a design comprising a single waveguide and one or more metallic nanostructures. The waveguide 106 may amplify the laser radiation 225 for better excitation of the plasmons. Plasmonic based techniques are also not limited by diffraction limit as in conventional optical systems. Thus, sub-diffraction limit confinement is possible. Low power operation is achieved since the combination of waveguide confinement due to the high-vertical-refractive-index-contrast of the waveguide 106 and the plasmonic enhancement due to metallic nanostructures produces sufficient intensity of the laser radiation 225 to simultaneously trap and generate SERS signal from the analyte(s) even at low power input laser radiation. High signal-to-noise ratio (SNR) is achieved since the metallic nanostructures produce very large optical forces that provide stable and very localized optical trapping of the analyte(s) which leads to much lower thermal drift, higher intensity, quenches the background florescence from the analyte(s) occurring at the same excitation wavelength thereby lowering the noise floor and longer integration time for collecting the Raman scattered radiation 226 from a single or multiple analytes. Further, plasmonic based techniques are non-specific and label-free. Moreover, visible wavelengths may be conveniently used as surface plasmons are strongly resonant at visible wavelengths. The enhancement in the field of laser radiation is also highly localised and may not damage any biological component in the analyte(s). In an embodiment, particles of the analyte(s) may also be transported to the metallic nanostructures by the inherently present radiation pressure of the guided light in the waveguide in conjunction with other various components, for example, microfluidic structures (not shown).

Figure 10:
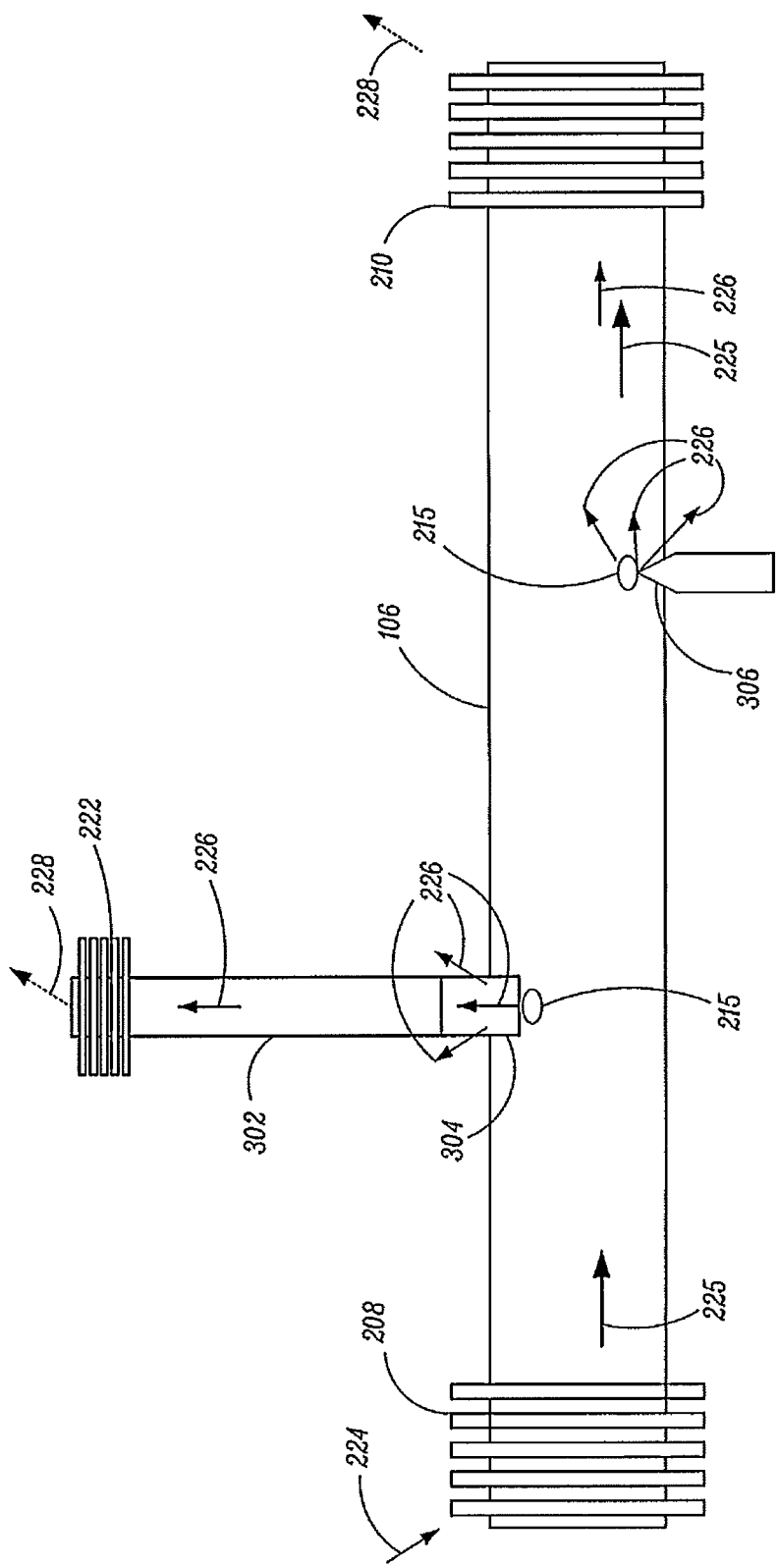
FIG. 10 shows a sectional view of the waveguide and the collection means, according to another embodiment of the present invention.

FIG. 10 shows the waveguide 106, and a collection means 302, according to another embodiment of the present invention (the integrating element is not shown in this figure, but it is to be understood that in this embodiment an integrating element according to one of the above described embodiments is provided). Gold nanotips 304 and 306 are embodied as nanostructures. The single particle 215 is trapped on each of the gold nanotips 304 and 306. However, in various other embodiments, several nanotips (not shown) may be used together to trap a single particle in order to increase the collection efficiency from the single particle. In an embodiment of the present invention, each of the gold nanotips 304 and 306 may have a dimension in a range from about a few nm to 100 nm.

The collection means 302 is disposed adjacent to the gold nanotip 304. The gold nanotip 304 couples radiation from the particle 215 to the collection means 302. Further, the grating coupler 222 is provided near the exit of the collection means 302. The grating coupler 222 can be configured to allow passage of Stokes wavelength and filter out the pump wavelength.

In operation, the gold nanotips 304 and 306 cause localised enhancement of the intensity of the laser radiation 225 due to surface plasmons. The Raman scattered radiation 226, from the particle 215 trapped on the gold nanotip 304, is collected by the collection means 302. The Stokes radiation 228 may be sent to the radiation analyser 108. Further, the Raman scattered radiation 226, from the particle 215 trapped on the gold nanotip 306, passes through the exit grating coupler 210. The exit grating coupler 210 is configured to allow passage of the Stokes radiation 228 and filter out the wavelength of the laser radiation 225. The Stokes radiation 228 from the exit grating coupler 210 may also be sent to the radiation analyser 108.

Figure 11:
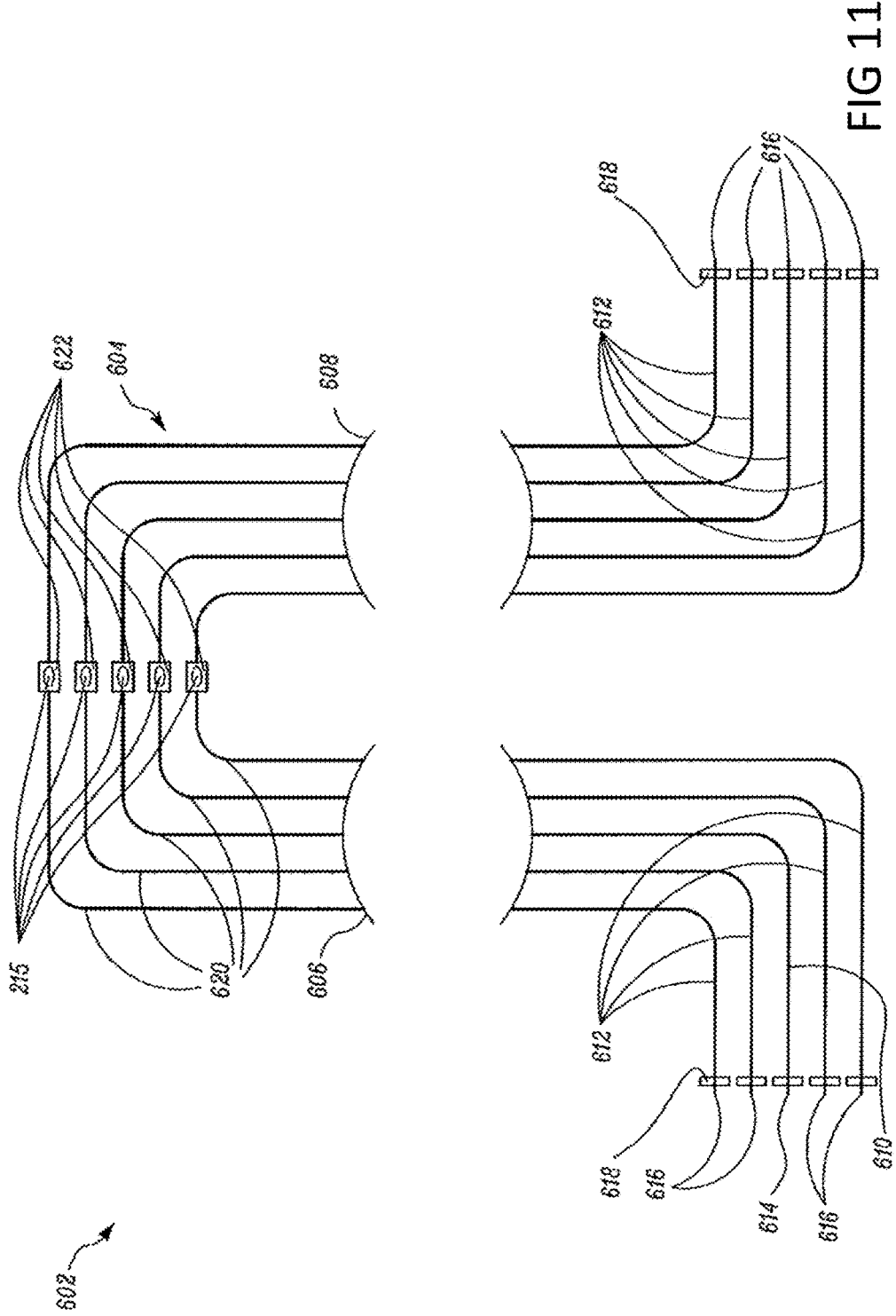
FIG. 11 shows a sectional view of the waveguide with an AWG section, according to an embodiment of the present invention.

FIG. 11 shows a waveguide 602, according to another embodiment of the present invention (an integrating element is not shown in this figure, but it is to be understood that in this embodiment an integrating element according to one of the above described embodiments may be provided). All the components of the waveguide 602 may be fully integrated in an on-chip configuration. The waveguide 602 comprises an Arrayed Waveguide Grating (AWG) section 604, a first slab region 606, a second slab region 608, an input waveguide 610 and multiple output waveguides 612. In another embodiment, multiple input waveguides may also be provided. The output waveguides 612 are provided on both sides of the AWG section 604. The input waveguide 610 comprises an input port 614 configured to receive laser radiation from the laser source 104. Further, each of the output waveguides 612 comprises an output port 616. Grating couplers 618 are provided on both ends at the input port 614 and the output ports 616.

The AWG section 604 comprises an array of waveguides 620. In various embodiments, the array of waveguides 620, the input waveguide 610, the output waveguides 612, the first slab region 606, and the second slab region 608 may be made of $Si_3N_4$. The waveguides 620 have different lengths. Further, a metallic nanostructure 622 is disposed on each waveguide 620. In various embodiments, the metallic nanostructures 622 may be nano-rods, nano-discs, nanotips etc. Each metallic nanostructure 622 traps the single particle 215 of the analyte. However, each metallic nanostructure 622 may also trap multiple particles.

In operation, the grating coupler 618 couples the laser radiation from the laser source 104 into the input port 614. Alternative coupling means such as a taper or butt coupling or other means may also be used to couple the laser light into the waveguide/chip. The laser radiation inside the input waveguide 610 enters the first slab region 606. The laser radiation may undergo divergence in the first slab region 606 and enters the waveguides 620 in the AWG section 604. The nanostructures 622, disposed on the waveguides 620, result in localised enhancement of the intensity of the laser radiation due to surface plasmons. The particles 215, trapped on the nanostructures 622, generate Raman scattered radiation. The lengths of the waveguides 620 in the AWG section 604 is such that the Stokes and Anti-Stokes radiation are focused at different regions of the output waveguides 612. Therefore, the Stokes and Anti-Stokes radiation are separated from the laser radiation. Consequently, a first group of the output ports 616 may output Stokes radiation, while a second group of output ports 616 may output Anti-Stokes radiation. Raman scattered radiation is collected from the output ports 616 at both sides of the AWG section 604. The grating couplers 618 and the AWG section 604 filter out the pump wavelength. Further, the grating couplers 618 also couple the Raman scattered radiation out of output ports 616. Stokes radiation may be analysed with a resolution in a range from about 0.1 nm to 0.5 nm.

In the aforementioned embodiments described with reference to FIGS. 1-11, various modifications (for example, in dimensions, shape, material etc.) may be made to maximise the enhancement due to surface plasmons. Further, various techniques in addition to SERS may also be used with the aforementioned embodiments. For example, Coherent anti-Stokes Raman Spectroscopy (CARS), Hyper-Raman Spectroscopy, stimulated Raman scattering (SRS) or the like may be used. In the case of CARS, three laser beams may be used: a pump beam, a Stokes beam, and a probe beam that is required to be coupled simultaneously. The structures used for plasmonic enhancement may be optimised in order to simultaneously enhance all the three laser beams leading to stable trapping of the analyte and generation of CARS signal from the trapped analyte. The CARS signal thus generated may be enhanced by a magnitude greater than in the case of SERS as CARS is a higher order technique using multiple laser beams. The CARS signal may therefore provide improved detection and/or analysis.

CARS involves the interaction of pump and Stokes beam through a non-linear process (third order susceptibility of the material) leading to the generation of strong coherent laser like CARS signal. This can be achieved in a waveguide configuration, for example as disclosed by Wijekoon et al., J. Phys. Chem., 97, 1065, 1993, to probe liquid analytes that is deposited on the waveguide surface. This is achieved by simultaneously coupling two beams into a waveguide through a prism and intense CARS is generated as a guided wave when 2 photons of pump ($f_p$) and 1 photon of stokes ($f_s$) signal interact in such a way that the difference ($2*f_p-f_s$) matches the Raman transitions (anti-Stokes) and is coupled out of the waveguide using another prism. The CARS signal is much stronger and sensitive than spontaneous Raman, and is efficient in rejecting any background florescence or luminescent background signal but still it is not strong and sensitive enough to probe analytes in very low concentrations. Therefore there is a need for further enhancing CARS signal that can be even stronger than SERS.

Figure 12:
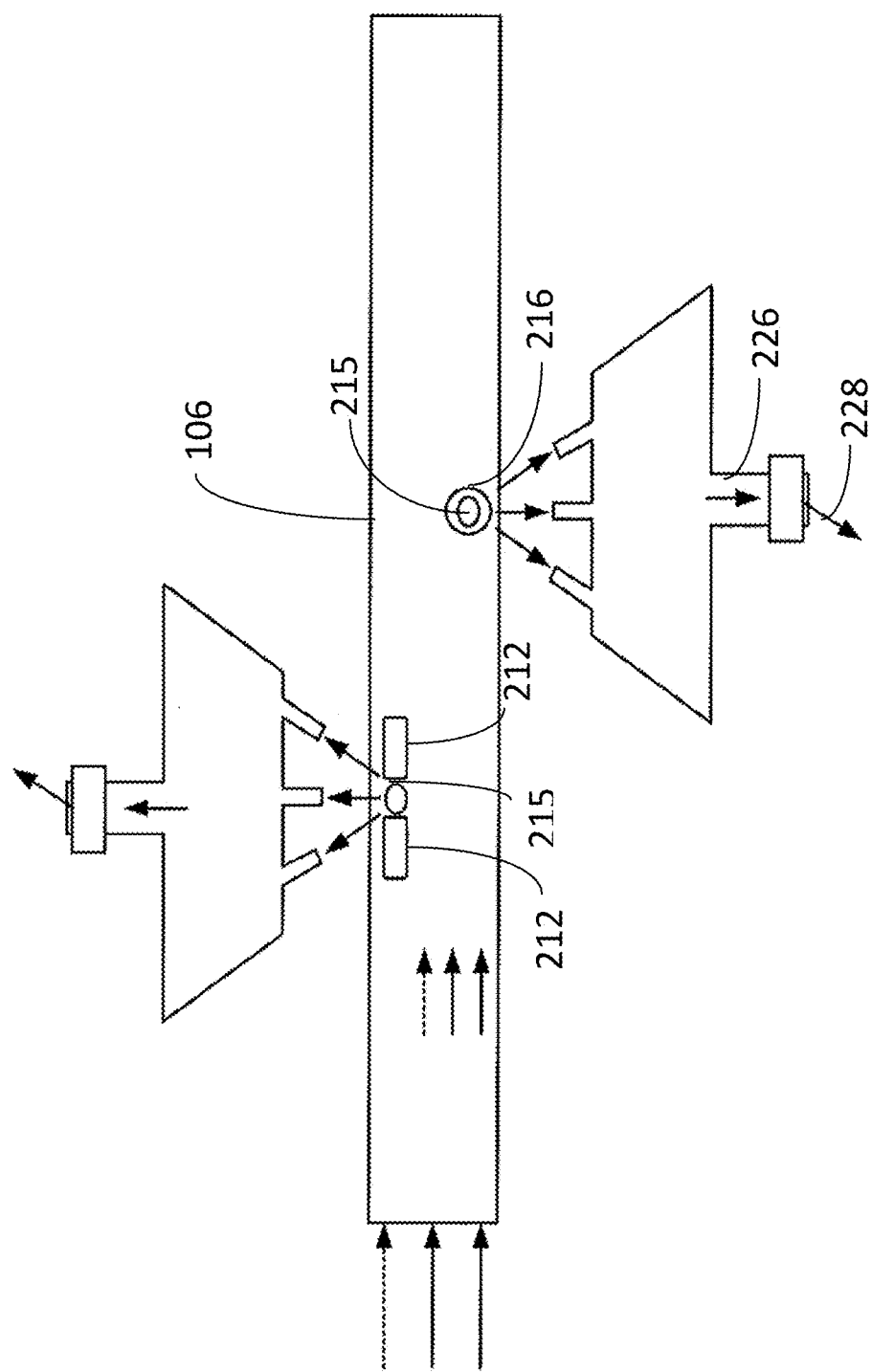
FIG. 12 shows a sectional view of a waveguide and collection means for a CARS based integrated device, according to an embodiment of the present invention.

In FIG. 12, two beams namely pump and Stokes beam are simultaneously coupled into the $Si_3N_4$ waveguide where they propagate together inside the waveguide (an integrating element is not shown in this figure, but it is to be understood that in this embodiment an integrating element according to one of the above described embodiments may be provided). On top of the waveguides appropriately designed metallic nanostructures are fabricated with sufficiently broad plasmon resonance such that all the three beams (pump, Stokes and anti-Stokes) involved in CARS are simultaneously in resonance when they interact with the metallic nanostructure. This leads to very strong enhancement of the CARS signal. The plasmonic design for three beams also leads to a very strong intensity gradient leading to efficient trapping of the analyte under the probe from which the CARS signal is generated. The strong florescence free plasmon enhanced CARS signal from the trapped analytes may be captured by the MMI waveguides based on $Si_3N_4$ and coupled out using grating couplers, leading to very sensitive and precise label-free detection of analytes.

The invention claimed is:
1. A molecular analysis device comprising:
a substrate;
a high-vertical-refractive-index-contrast waveguide on the substrate comprising a coupling means configured for coupling a predetermined frequency or range of frequencies of laser radiation into the waveguide and comprising a planar integrating element with a filter or reflector element adjacent to the integrating element arranged for reflecting said laser radiation, the waveguide and the planar integrating element having a height such that they are single mode out-of-plane;
a metallic nanostructure disposed on top of or adjacent to the planar integrating element, positioned for being irradiated by said laser radiation coupled into the waveguide as well as said laser radiation reflected by said filter or reflector element, and configured such that the field intensity and the gradient of said laser radiation that is coupled into the guided mode of the waveguide, are enhanced over a volume around the nanostructure to cause both plasmonic based optical trapping of analytes in a medium and plasmonic based excitation of said particles to produce Raman scattered radiation; and
a Raman scattered radiation collection means disposed on the substrate for collecting said Raman scattered radiation produced by said particles.

2. A molecular analysis device according to claim 1, wherein said planar integrating element is a broadened part of the waveguide and said filter or reflector element is provided along the periphery of the planar integrating element.

3. A molecular analysis device according to claim 2, wherein said planar integrating element is one of the following: a disc, a disc segment, an oval-shaped disc, a polygonal element.

4. A molecular analysis device according to claim 2, wherein said filter or reflector element along the periphery of the planar integrating element is one of the following: a distributed Bragg reflector, a metallic mirror, a single interface between the waveguide and an outer lateral cladding due to a difference in refractive index of the waveguide and the refractive index of the outer cladding.

5. A molecular analysis device according to claim 1, wherein the planar integrating element is a section of the waveguide and wherein said filter or reflector element is an inline filter or an internal reflection mirror.

6. A molecular analysis device according to claim 1, wherein said metallic nanostructure is configured on top of the planar integrating element for transforming the guided mode of the waveguide to an intensity profile that forms a stable trap by overcoming the random Brownian motion requiring a potential energy barrier of at least $10k_bT$, wherein $k_b$ is the Boltzmann's constant and T is the temperature of the medium.

7. A molecular analysis device according to claim 1, further comprising a laser source disposed on the substrate and configured for generating said laser radiation.

8. A molecular analysis device according to claim 1, wherein a radiation analyser is disposed on the substrate and configured for analysing said collected Raman scattered radiation.

9. A molecular analysis device according to claim 1, wherein the coupling means is a grating coupler.

10. A molecular analysis device according to claim 1, wherein the collection means comprises an optical structure disposed adjacent to said metallic nanostructure.

11. A molecular analysis device according to claim 1, wherein the collection means comprises a second waveguide connecting to the planar integrating element and comprising a grating coupler designed for Stokes wavelength.

12. A molecular analysis device according to claim 1, wherein the waveguide comprises an AWG section where the metallic nanostructure is disposed, the AWG length being configured such that the Stokes and Anti-Stokes wavelengths are focused at different regions of the waveguide, and wherein the waveguide comprises grating couplers at both ends to couple said laser radiation into said waveguide and said Raman scattered radiation out of said waveguide.

13. A molecular analysis device according to claim 1, wherein the metallic nanostructure comprises one or more of nano-rods, nano-discs, nanotips, nano-voids or apertures, or metallic nanoparticles in a colloidal suspension.

14. Method for molecular analysis of an analyte, comprising the steps of:
a) immersing a molecular analysis device in the analyte or suspending analyte in a solution on top of the molecular analysis device, the molecular analysis device comprising:
a substrate;
a high-vertical-refractive-index-contrast waveguide on the substrate comprising a planar integrating element with a filter or reflector element adjacent to the integrating element, the waveguide and the planar integrating element having a height such that they are single mode out-of-plane, and comprising a coupling means configured for coupling a predetermined frequency or range of frequencies of laser radiation into the waveguide;
a metallic nanostructure disposed on top of or adjacent to the planar integrating element, positioned for being irradiated by said laser radiation coupled into the waveguide as well as said laser radiation reflected by said filter or reflector element, and configured such that the field intensity and its gradient of said laser radiation that is coupled into the guided mode of the waveguide, are enhanced over a volume around the nanostructure to cause both plasmonic based optical trapping of analytes in a medium and plasmonic based excitation of said particles to produce Raman scattered radiation;
a Raman scattered radiation collection means disposed on the substrate for collecting said Raman scattered radiation produced by said particles;
b) irradiating said molecular analysis device with laser radiation, such that said predetermined range or frequency of laser radiation is coupled into said waveguide and causes said plasmonic based optical trapping of particles from the analyte and plasmonic based excitation of said particles to produce Raman scattered radiation;
c) collecting by means of said collection means the Raman scattered radiation produced by said particles; and
d) analysing said collected Raman scattered radiation.

15. Method according to claim 14, wherein said metallic nanostructure is configured for transforming the underlying guided mode to an intensity profile that forms a stable trap by overcoming the random Brownian motion requiring a potential energy barrier of at least $10k_bT$, wherein $k_b$ is the Boltzmann's constant and T is the temperature at the particles/metallic nanostructure interface.

* * * * *